United States Patent [19]
Card

[11] Patent Number: 4,978,803
[45] Date of Patent: Dec. 18, 1990

[54] VAPOR PHASE OXIDATION PROCESS FOR MAKING GLYOXAL

[75] Inventor: Roger J. Card, Stamford, Conn.

[73] Assignee: American Cyanamid Company, Stamford, Conn.

[21] Appl. No.: 373,843

[22] Filed: Jun. 26, 1989

[51] Int. Cl.$^5$ .................. C07C 45/38; C07C 45/39
[52] U.S. Cl. .................... 568/486; 568/471; 568/473; 568/485
[58] Field of Search ............ 568/471, 473, 486, 485

[56] References Cited

U.S. PATENT DOCUMENTS

| | | | |
|---|---|---|---|
| 3,948,997 | 4/1976 | Howe et al. | 568/473 |
| 4,098,826 | 7/1978 | Alpers et al. | 568/473 |
| 4,198,351 | 4/1980 | Branecky et al. | 568/471 |
| 4,258,216 | 3/1981 | Trecek et al. | 568/473 |
| 4,503,261 | 3/1985 | Sauer et al. | 568/471 |

*Primary Examiner*—Werren B. Lone
*Attorney, Agent, or Firm*—Gordon L. Hart

[57] ABSTRACT

In the process for making glyoxal by catalytic oxidation of ethylene glycol in contact with catalyst comprising copper, glyoxal yield is improved and catalyst life is improved by the presence of a small amount of iodine or organic iodide in the reactant feed mixture.

8 Claims, No Drawings

VAPOR PHASE OXIDATION PROCESS FOR MAKING GLYOXAL

The invention relates to improvements in a process for preparing glyoxal from ethylene glycol. More particularly, it relates to improving the vapor phase oxidation process wherein ethylene glycol is oxidized to glyoxal in the presence of a catalyst containing copper, preferably with silver and in some cases other minor ingredients.

U.S. Pat. No. 3,948,997 described a process for vapor phase oxidation of ethylene glycol to form glyoxal by reaction of ethylene glycol and oxygen in a diluted vapor feed. The feed contains one to four mols oxygen per mol glycol and preferably about 40 to 60 mols of inert diluent gas per mol oxygen. The reaction is carried out in the presence of certain catalysts which contain one or more metals selected from copper, silver and gold and which may also contain elements from Group IVb and group Vb of the periodic table Copper and silver are preferred metals for the catalyst and phosphorous is a preferred promoter. The same patent described examples of processes producing very high conversion of ethylene glycol with fair yields of glyoxal and substantial production of undesired by-products. The reaction temperature may be in the range from 180°-600° C. One object of the present invention is to improve yields of glyoxal in a process like those described while maintaining conversion of ethylene glycol at very high level An earlier vapor phase oxidation process for production of glyoxal employing a catalyst containing copper was described in U.S. Pat. Nos. 2,339,283 and 2,339,346. The yield of glyoxal was improved by addition of a small amount (e.g., 0.02% or 200 ppm of gas mixture) of ethylene dichloride in the gas mixture being oxidized U.S. Pat. No. 4,258,216 described a process for preparing glyoxal from ethylene glycol in the presence of a copper based catalyst by addition of a bromine compound to the gaseous feed mixture Use of bromine compounds in this manner improves yield but it has been found to cause loss of catalyst life. Another object of the invention is to obtain improved glyoxal yields while maintaining longer catalyst life.

We discovered that addition of small amounts of iodine or a compound of iodine or a mixture thereof to the reactant stream in a vapor phase oxidation process of the kind described results in improved glyoxal yields, at least as good as those obtained with bromine compounds. Also, the use of iodine additives instead of bromine additives can significantly increase catalyst life.

Iodine is the most preferred additive for use in accordance with the invention. Iodine compounds are also suitable for the use. Such compounds include iodoalkanes having 1-8 carbon atoms such as methyl iodide, methylene iodine, iodoform, ethyl iodide, an aryl iodide such as phenyl iodide and the like. The most preferred iodine compounds are organic iodides which are soluble in ethylene glycol and can be readily vaporized at temperature below 400° C., preferably below 270° C. Ethyl iodide is an especially preferred additive.

The amount of iodine or iodine compound to be added in the gaseous feed mixture which is fed to the catalytic reactor is an amount sufficient for significantly increasing the yield of glyoxal, as compared with operation without the iodine or iodine compound. Usually, an effective minimum concentration will be about 0.5 parts by weight of the iodine or iodine compound per million parts of the gaseous feed mixture. Excess concentration of iodine or compound of iodine in the feed mixture may decrease glyoxal yield and increase glycol aldehyde formation While the maximum concentration useable without such disadvantage will depend to some extent upon the selected specific operating conditions, as well as the specific iodine additive selected, such maximum concentration will usually be about 25 parts by weight of the iodine additive per million parts of gaseous mixture. Optimum results will usually be attained using a concentration in the range from 0.5 to 25 ppm additive in the feed mixture and most usually in the range from 1 to 15 ppm.

The catalytic process to which the improvement of this invention relates, including variations in reactants, ratios of reactants, catalyst compositions and the like are known and have been described in prior art as, for example, in the patents mentioned above, and particularly in U.S. Pat. No. 3,948,997. Details of a most preferred embodiment are included in the examples below.

The invention may be used to advantage in processes using any of the catalysts described in U.S. Pat. No. 3,948,997, which catalysts comprise one or more metals from Group I B, e.g. copper, silver and gold and may further comprise one or more Group IV B elements, e.g. germanium, tin, lead, preferably as the oxide, and may further comprise one or more Group V B elements such as nitrogen, phosphorus, arsenic, antimony and bismuth Preferred catalysts comprise copper and phosphorus and may also comprise silver. Silver may be present in amounts from zero up to about 25% by wt of the catalyst, and phosphorus may be present in amounts up to about 20% by wt of the catalyst, the remainder being copper. An especially preferred catalyst is an alloy of copper containing 5-15% by wt of silver and 1-10% by wt of phosphorus.

The catalyst may be in any of the physical forms described in said patent, such as alloy in the form of turnings, gauze, etc., intimate particulate mixture of the essential constituents of the catalyst, or supported on inorganic support material, etc. A preferred form for use of the catalyst is a mixture of the active metallic catalyst with an inert ceramic diluent, such as ceramic pellets, saddles, or other shapes. A preferred mixture. is an approximately equivolume mixture of active catalyst and inert ceramic diluent While not wishing to be bound by theory, there appear to be two principal reasons why the use of iodine or its compounds instead of bromine or its compounds can improve catalyst life. First, copper(I) appears to be the active catalyst for dehydrogenation processes. While bromine compounds or chlorine compounds can react with copper to form a mixture of copper(I) and copper(1II) species, only copper(I) iodide appears to be formed from the reaction of copper with iodine or its compounds. Therefore, iodine or its compounds are more efficient in forming the active catalytic species. Second, under typical reaction conditions (eg. ~500° C.) copper bromides (mpt 492° C. for CuBr and 498° C. for $CuBr_2$) and copper(I) chloride (mpt 430° C.) are expected to be in the liquid or molten state. Droplets of these liquids can be easily eroded from the catalyst surface and carried into the gaseous reactant stream The droplets of molten copper salts in the reactant stream are oxidized under conditions in the reactor to yield small particles of copper oxides which deposit in the flow channels of the reactor. As the flow channels become clogged with copper oxide powder the pressure drop across the catalyst bed increases. When the pressure drop becomes too great, the reactor must be shut down and the catalyst bed changed In contrast to the behavior of the copper bromides and chlorides, copper iodide melts at 605° C., well above the reaction temperatures ordinarily used in the process. Since it is not molten, copper iodide will not be so readily eroded from the catalyst surface. As a result, much longer catalyst lifetimes can be obtained.

Following are detailed descriptions of specific examples, including our most preferred mode of carrying out the invention. Also included are examples for comparison to illustrate some of the advantages of the invention.

In each example, oxygen was supplied as air which also supplied nitrogen as an inert gas diluent in the reactant feed stream. More diluent inert gas can be added as needed from recycle gas not condensed in the product gas scrubber In each of the following examples aqueous ethylene glycol (1.37 mol $H_2O$/ mol glycol) is vaporized in a heated stainless steel pipe filled with Pyrex® glass beads. Additives are dissolved in and vaporized with the aqueous glycol feed. The level of additives is reported in the tables as ppm of additive on total weight of the feed mixture fed to the reaction The glycol vapor is mixed into a stream of nitrogen which is then mixed with preheated air. This feed gas mixture is then led to a Vycor glass reactor packed with a bed of metallic catalyst. The packed bed contains 135 g of metallic catalyst particles. Composition of the metal is an alloy containing 10% silver, 2.5% phosphorus, and the remainder of copper. The reactor is equipped with thermowells for temperature measurement in the reactor bed. The reactor is placed in a fluidized hot sand bath which is used for controlling temperature in the reactor.

The feed gas mixture is introduced at the reactor inlet at a glycol feed rate of 21 g/hr and the ratio of inert gas to glycol in the feed mixture is maintained at 50 mol inert gas per mol glycol. Ratios of oxygen to ethylene glycol in the feed streams were varied and are reported in the tables separately for each example. Vapor lines to and from the reactor are maintained at temperature of 250°–270° C. Temperature in the reactor is maintained at 415°–500° C. Pressure in the reactor is not critical and is usually maintained at a pressure in the range from 1 to 3 atmospheres. In the reactor, the reactant vapors contact the catalyst as the feed gas mixture traverses the catalyst bed. Residence time in the reactor may vary depending on the feed gas composition. A typical residence time is about 1.6 sec.

On leaving the reactor, the product vapor stream can be directed either to waste scrubbers where products are condensed and the waste gas is vented, or to a sampling system where the products are scrubbed in chilled water, then further condensed in a series of dry-ice traps. In the sampling system, the uncondensed gas stream is sampled for CO, $CO_2$, and $O_2$ using a gas chromatograph and an electrochemical oxygen analyzer. The total condensate is weighed and analyzed. Glyoxal, formaldehyde and the total acidity are measured by a series of titrations, while the ethylene glycol and glycol aldehyde are measured using a gas chromatograph. The reactor is operated at stated conditions to steady running, whereupon the product is diverted to the sampling system for analysis.

EXAMPLES 1–6

Data from comparative runs using bromine compound additives and iodine compound additives are presented in Table I. The data are obtained from the sequential use of these additives over the same bed of catalyst. Examples 2 & 6 present data for the bromine compound control. Examples 1, 3, 4, and 5 show the use of a variety of iodine compounds used to obtain product yields equivalent to those from the control.

EXAMPLES 7–10

Examples 7–9 in Table II show that glyoxal yields are relatively constant as the level of ethyl iodide additive is increased from 3 to 12 ppm. Example 10 shows that the glyoxal yield decreased and glycol aldehyde yield increased when 24 ppm ethyl iodide was used.

EXAMPLE 11–18

The effect of oxygen-ethylene glycol ratio on product yields was determined for two different iodine compound additives. In Examples 11–13, Table III, glyoxal yield increased and glycol aldehyde yield decreased as the $O_2$/EG ratio was increased from 1.14 to 1.19: Examples 12 and 13 give higher glyoxal yields and lower glycol aldehyde yields than the bromoform control runs (Examples 2 & 6). This demonstrates that iodine compounds can give a superior product to that obtained with the bromoform control.

Examples 14–18 in Table IV demonstrate that $O_2$/EG ratios greater than 1.20 were not optimum under the conditions used. Comparison of examples 13 and 16 demonstrates that optimization of $O_2$/EG level may vary depending on the specific iodine compound used.

EXAMPLES 19–23

Examples 19–23 demonstrate that yields are sensitive to reaction temperature.

EXAMPLES 24–28

Examples 24–28 demonstrate that glyoxal yields as high as 83% can be obtained using iodine additive. This is a surprising improvement as compared with the bromine compound controls.

TABLE I

USE OF IODO COMPOUNDS OVER FRESH CATALYST BED[a]

| Example No. | Additive | Et Glycol Conv (%) | Product Yields % | | | | |
|---|---|---|---|---|---|---|---|
| | | | Glyoxal | Formaldehyde | Glycol Aldehyde | Acids | CO + $CO_2$ |
| 1 | $H_2CI_2$ (8 runs) | 98 | 76 | 4 | 1.3 | .4 | 15 |
| 2 | $HCBr_3$ (4 runs) | 98 | 79 | 3 | 1.5 | .4 | 13 |
| 3 | $HCI_3$ (4 runs) | 96+ | 77 | 4 | 1.6 | .4 | 13 |
| 4 | $H_2CI_2$ (3 runs) | 97+ | 78 | 3 | 2.3 | .4 | 13 |
| 5 | $C_2H_5I$ | 98+ | 79 | 3 | 1.2 | <.4 | 13 |

TABLE I-continued

USE OF IODO COMPOUNDS OVER FRESH CATALYST BED[a]

| Example No. | Additive | Et Glycol Conv (%) | Product Yields % | | | | |
|---|---|---|---|---|---|---|---|
| | | | Glyoxal | Formaldehyde | Glycol Aldehyde | Acids | CO + CO$_2$ |
| 6 | (3 runs) HCBr$_3$ (2 runs) | 97+ | 78 | 3 | 2.3 | <.4 | 13 |

[a] Additives used sequentially over one bed of catalyst. O$_2$/Et Glycol = 1.14; 3 ppm additive; 470–490° C.; yields based on glycol converted, normalized to 100% C Balance.

TABLE II

EFFECT OF ETHYL IODIDE LEVEL ON PRODUCT YIELDS[a]

| Example No. | C$_2$H$_5$I Level (ppm) | Et Glycol Conv (%) | Product Yields % | | | | |
|---|---|---|---|---|---|---|---|
| | | | Glyoxal | Formaldehyde | Glycol Aldehyde | Acids | CO + CO$_2$ |
| 7 | 3 | 98+ | 79 | 3 | 1.2 | <.4 | 13 |
| 8 | 6 | 99 | 78 | 3.3 | 1.1 | <.4 | 16 |
| 9 | 12 | 99 | 80 | 2.9 | 1.2 | .4 | 14 |
| 10 | 24 | 99 | 75 | 3.5 | 5.4 | <.4 | 15 |

[a] O$_2$/Et Glycol = 1.14; 470–490° C.; yields based on glycol converted, normalized to 100% C Balance.

TABLE III

EFFECT OF O$_2$/ET GLYCOL ON PRODUCT YIELDS WITH 3 ppm CH$_2$I$_2$ ADDITIVE[a]

| Example No. | O$_2$/Et Glycol | Et Glycol Conv (%) | Product Yields % | | | | |
|---|---|---|---|---|---|---|---|
| | | | Glyoxal | Formaldehyde | Glycol Aldehyde | Acids | CO + CO$_2$ |
| 11 | 1.14 (3 runs) | 97 | 78 | 3 | 2.3 | <.4 | 13 |
| 12 | 1.17 (1 run) | 99 | 80 | 3.3 | 1.2 | <.4 | 14 |
| 13 | 1.19 (1 run) | 99 | 81 | 3.1 | 0.9 | <.4 | 14 |

[a] 470–490° C.; yields based on glycol converted, normalized to 100% Balance.

TABLE IV

EFFECT OF O$_2$/ET GLYCOL ON PRODUCT YIELDS WITH ETHYL IODIDE ADDITIVE[a]

| Example No. | O$_2$/Et Glycol | Et Glycol Conv (%) | Product Yields % | | | | |
|---|---|---|---|---|---|---|---|
| | | | Glyoxal | Formaldehyde | Glycol Aldehyde | Acids | CO + CO$_2$ |
| 14 | 1.14 (5 runs) | 98+ | 79 | 3.2 | 1.3 | .4 | 14 |
| 15 | 1.17 (2 runs) | 99+ | 78 | 3.3 | 0.9 | .4 | 16 |
| 16 | (1.19) (2 runs) | 98 | 74 | 4 | 2 | .4 | 18 |
| 17 | 1.21 | 99 | 74 | 4 | 1.4 | .4 | 19 |
| 18 | 1.26 | 99 | 71 | 2 | 1.8 | .4 | 24 |

[a] 470–490° C.; 3 ppm ethyl iodide; yields based on glycol converted, normalized to 100% C Balance.

TABLE V

EFFECT OF REACTION TEMPERATURE ON YIELDS USING ETHYL IODIDE AND O$_2$/ET GLYCOL = 1.17

| Example No | Temp (°C.) | Et Glycol Conv (%) | Product Yields % | | | | |
|---|---|---|---|---|---|---|---|
| | | | Glyoxal | Formaldehyde | Glycol Aldehyde | Acids | CO + CO$_2$ |
| 19 | 415 | 95 | 69 | 3.3 | 4 | .4 | 19 |
| 20 | 428 | 95 | 67 | 4.2 | 5 | .4 | 19 |
| 21 | 435 | 97 | 69 | 3.3 | 3 | .4 | 21 |
| 22 | 435 | 95 | 67 | 4.5 | 4 | .4 | 18 |
| 23 | 460 | 97 | 76 | 4.3 | 1 | .4 | 15 |

TABLE VI

USE OF IODINE ADDITIVE[a]

| Example No | Temp (°C.) | Et Glycol Conv (%) | Normalized Product Yields % | | | | |
|---|---|---|---|---|---|---|---|
| | | | Glyoxal | Formaldehyde | Glycol Aldehyde | Acids | CO + CO$_2$ |
| 24 | 490 | 99 | 81 | 4.7 | 1.0 | <.4 | 10.5 |
| 25 | 495 | 97 | 81 | 3.6 | 0.7 | <.4 | 12 |
| 26 | 470 | 96 | 82 | 3.4 | 2.2 | <.4 | 8.4 |
| 27 | 485 | 98 | 83 | 3.3 | 1.4 | .5 | 10.2 |

TABLE VI-continued

| | | | USE OF IODINE ADDITIVE[a] | | | | |
|---|---|---|---|---|---|---|---|
| Example No | Temp (°C.) | Et Glycol Conv (%) | Normalized Product Yields % | | | | |
| | | | Glyoxal | Formaldehyde | Glycol Aldehyde | Acids | CO + CO$_2$ |
| 28 | 465 | 99 | 83 | 2.7 | .9 | <.4 | 11.3 |

[a]$O_2$/Et Glycol = 1.17; 3 ppm I$_2$

We claim:

1. In the process for oxidation of ethylene glycol to produce glyoxal wherein a vapor phase mixture comprising oxygen, ethylene glycol and inert diluent gas is contacted with a solid catalyst consisting essentially of 0 to 25% by weight silver, up to 20% by weight of phosphorus and the remainder being copper at reaction temperature in the range from 180° C. to 600° C., the improvement wherein said vapor phase mixture further comprises from 0.5 to 25 ppm of an additive selective from iodine and organic compounds of iodine soluble in ethylene glycol and readily vaporized at temperature below 400° C. and reactive with copper under the reaction conditions to form iodide of copper.

2. A process defined by claim 1 wherein the selected additive is iodine.

3. A process defined by claim 1 wherein the selected additive is an iodide of an alkane having 1 to 8 carbon atoms and 1 to 3 iodine atoms.

4. A process defined by claim 1 wherein the catalyst is an alloy of copper containing 5-15% by wt silver and 1-10% by wt phosphorus.

5. A process defined by claim 4 wherein the selected additive is iodine.

6. A process defined by claim 3 wherein the selected additive is ethyl iodide.

7. A process defined by claim 3 wherein the selected additive is triiodomethane.

8. A process defined by claim 3 wherein the selected additive is diiodomethane.

* * * * *